US010036697B2

(12) United States Patent
Fox et al.

(10) Patent No.: US 10,036,697 B2
(45) Date of Patent: Jul. 31, 2018

(54) FLOW RATE BALANCED, DYNAMICALLY ADJUSTABLE SHEATH DELIVERY SYSTEM FOR FLOW CYTOMETRY

(71) Applicant: Bio-Rad Laboratories, Inc., Hercules, CA (US)

(72) Inventors: Daniel Nelson Fox, Bellvue, CO (US); Nathan Michael Gaskill-Fox, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 44 days.

(21) Appl. No.: 15/376,504

(22) Filed: Dec. 12, 2016

(65) Prior Publication Data

US 2017/0160186 A1 Jun. 8, 2017

Related U.S. Application Data

(62) Division of application No. 13/918,156, filed on Jun. 14, 2013, now Pat. No. 9,551,637.
(Continued)

(51) Int. Cl.
*G01N 1/28* (2006.01)
*G01N 15/14* (2006.01)
(Continued)

(52) U.S. Cl.
CPC ........... *G01N 15/1404* (2013.01); *G01N 1/28* (2013.01); *G01N 2015/0065* (2013.01);
(Continued)

(58) Field of Classification Search
CPC ................ G01N 1/28; G01N 15/1404; G01N 2015/1406; Y10T 137/7287;
(Continued)

(56) References Cited

U.S. PATENT DOCUMENTS 3,826,364 A  7/1974 Bonner et al.
4,284,210 A  8/1981 Horak
(Continued)

FOREIGN PATENT DOCUMENTS

CN  1085330   4/1994
CN  1767891   5/2006
(Continued)

OTHER PUBLICATIONS

U.S. Appl. No. 15/417,131, dated Jan. 26, 2017, Fox et al.
(Continued)

*Primary Examiner* — Michael R Reid
*Assistant Examiner* — Christopher Ballman
(74) *Attorney, Agent, or Firm* — Weaver Austin Villeneuve & Sampson LLP (57) ABSTRACT

Disclosed is a sheath delivery system that uses a continuous flow of sheath fluid into a pressurized internal reservoir that substantially matches the outflow of sheath fluid through the nozzle of a flow cytometer. A substantially constant level of the sheath fluid is maintained. If the sheath fluid level falls below a desired level, or goes above a desired level, a dampened control system is used to reach the desired level. In addition, air pressure in the pressurized internal container is controlled so that an external sheath container can be removed and refilled with additional sheath fluid without stopping the sheath delivery system 100. Differences in pressure are detected by a droplet camera, which measures the droplet breakoff point to determine the pressure of the sheath fluid in the nozzle.

19 Claims, 3 Drawing Sheets

Related U.S. Application Data (60) Provisional application No. 61/659,528, filed on Jun. 14, 2012.

(51) Int. Cl.
    *G01N 15/10* (2006.01)
    *G01N 15/00* (2006.01)

(52) U.S. Cl.
    CPC ........... *G01N 2015/1006* (2013.01); *G01N 2015/1406* (2013.01); *G01N 2015/1409* (2013.01); *Y10T 137/0324* (2015.04); *Y10T 137/7287* (2015.04); *Y10T 137/7303* (2015.04); *Y10T 137/85978* (2015.04)

(58) Field of Classification Search
    CPC ....... Y10T 137/7303; Y10T 137/85978; Y10T 137/0324
    See application file for complete search history.

(56) References Cited

U.S. PATENT DOCUMENTS

| | | | |
|---|---|---|---|
| 5,641,457 | A | 6/1997 | Vardanega et al. |
| 5,915,925 | A | 6/1999 | North, Jr. |
| 6,183,697 | B1 | 2/2001 | Tanaka et al. |
| 6,200,101 | B1 | 3/2001 | North, Jr. |
| 6,372,506 | B1 | 4/2002 | Norton |
| 7,242,474 | B2 | 7/2007 | Cox et al. |
| 7,776,268 | B2 | 8/2010 | Rich |
| 8,004,674 | B2 | 8/2011 | Ball et al. |
| 8,229,684 | B2 | 7/2012 | Goebel et al. |
| 8,564,776 | B2 | 10/2013 | Graves et al. |
| 9,551,637 | B2 | 1/2017 | Fox et al. |
| 2002/0154567 | A1 | 10/2002 | Husher |
| 2002/0192113 | A1 | 12/2002 | Uffenheimer et al. |
| 2004/0031521 | A1 | 2/2004 | Vrane et al. |
| 2005/0019949 | A1 | 1/2005 | Hall et al. |
| 2005/0219945 | A1 | 10/2005 | Kelley et al. |
| 2008/0182056 | A1 | 7/2008 | Bakker et al. |
| 2010/0018584 | A1 | 1/2010 | Bransky et al. |
| 2010/0319469 | A1 | 12/2010 | Rich |
| 2011/0221892 | A1 | 9/2011 | Neckels et al. |
| 2012/0070818 | A1 | 3/2012 | Rowlen et al. |
| 2012/0097582 | A1 | 4/2012 | Tsukii et al. |
| 2012/0308436 | A1* | 12/2012 | Kanda ............... G01N 15/1404 422/73 |
| 2013/0333765 | A1 | 12/2013 | Fox et al. |
| 2013/0343149 | A1 | 12/2013 | Fox et al. |

FOREIGN PATENT DOCUMENTS

| | | |
|---|---|---|
| CN | 201880510 U | 6/2011 |
| EP | 2 224 224 A2 | 9/2010 |
| WO | WO 2004/088283 A2 | 10/2004 |
| WO | WO 2009/026919 A2 | 3/2009 |
| WO | WO 2013/188770 A1 | 12/2013 |
| WO | WO 2013/192401 A1 | 12/2013 |

OTHER PUBLICATIONS

U.S. Office Action dated Sep. 22, 2015 issued U.S. Appl. No. 13/918,156.
U.S. Final Office Action dated Feb. 22, 2016 issued in U.S. Appl. No. 13/918,156.
U.S. Office Action dated May 26, 2016 issued in U.S. Appl. No. 13/918,156.
U.S. Notice of Allowance dated Sep. 28, 2016 issued in U.S. Appl. No. 13/918,156.
U.S. Notice of Allowance [Corrected Notice of Allowability] dated Oct. 18, 2016 issued in U.S. Appl. No. 13/918,156.
U.S. Office Action dated Mar. 3, 2016 issued in U.S. Appl. No. 13/922,635.
U.S. Notice of Allowance dated Sep. 23, 2016 issued in U.S. Appl. No. 13/922,635.
U.S. Notice of Allowance dated Oct. 27, 2016 issued in U.S. Appl. No. 13/922,635.
U.S. Notice of Allowance dated Feb. 15, 2017 issued in U.S. Appl. No. 15/417,131.
PCT International Search Report and Written Opinion, dated Nov. 14, 2013, issued in PCT/US2013/045902.
PCT International Preliminary Report on Patentability and Written Opinion, dated Dec. 24, 2014, issued in PCT/US2013/045902.
Chinese First Office Action dated Jan. 29, 2016 issued in CN 201380030535.7.
Chinese Second Office Action dated Dec. 20, 2016 issued in CN 201380030535.7.
European Extended Search Report dated Jan. 7, 2016 issued in EP 13 80 4145.4.
PCT International Search Report and Written Opinion, dated Nov. 15, 2013, issued in PCT/US2013/046774.
European Extended Search Report dated Feb. 5, 2016 issued in EP 13 80 6142.9.
Chinese First Office Action dated Jun. 2, 2016 issued in CN 201380032476.7.

\* cited by examiner

FLOW RATE BALANCED, DYNAMICALLY ADJUSTABLE SHEATH DELIVERY SYSTEM FOR FLOW CYTOMETRY

CROSS-REFERENCE TO RELATED APPLICATION

This application is a divisional application of U.S. patent application Ser. No. 13/918,156, filed on Jun. 14, 2013, entitled "Flow Rate Balanced, Dynamically Adjustable Sheath Delivery System for Flow Cytometry," which claims the benefit under 35 U.S.C. § 119(e) to U.S. Provisional Patent Application No. 61/659,528, filed Jun. 14, 2012, entitled "Flow Rate Balance, Dynamically Adjustable Sheath Delivery System for Flow Cytometry," which are both incorporated herein by reference for all that they disclose and teach.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest. Sorting and analysis of these particles can provide valuable information to both researchers and clinicians. In addition, sorted particles can be used for various purposes to achieve a wide variety of desired results.

SUMMARY

An embodiment of the present invention may therefore comprise a method of controlling pressure of a sheath fluid in a pressurized container in a flow cytometer comprising: continuously pumping the sheath fluid from an external container into the pressurized container to attempt to maintain a substantially constant sheath fluid level in the pressurized reservoir so that an in-flow rate of sheath fluid flowing into the pressurized reservoir is substantially equal to an out-flow rate of the sheath fluid flowing out of the pressurized reservoir; adjusting the in-flow rate of the sheath fluid flowing into the pressurized reservoir whenever the substantially constant sheath fluid level changes.

An embodiment of the present invention may further comprise a method of replacing an external sheath container while continuously operating a sheath fluid system in a flow cytometer comprising: substantially matching an output flow rate of an internal reservoir of sheath fluid flowing through a nozzle with an input flow rate of an input flow of sheath fluid from the external sheath container to the internal sheath container to substantially maintain a preselected level of sheath fluid in the internal reservoir; stopping the input flow of the sheath fluid while the external sheath container is removed; increasing air pressure in the internal reservoir while the input flow of the sheath fluid is stopped to substantially maintain a constant pressure on the sheath fluid through the nozzle; replacing the external sheath container; pumping sheath fluid from the external sheath container to the internal reservoir at an input flow rate that is greater than the output flow rate until the sheath fluid in the internal reservoir reaches the preselected level; reducing the air pressure in the internal reservoir while the internal reservoir is being filled to the preselected level to maintain a substantially constant pressure on the sheath fluid flowing through the nozzle.

An embodiment of the present invention may further comprise a sheath fluid system for supplying sheath fluid in a flow cytometer at a substantially constant pressure comprising: an internal pressurized sheath fluid reservoir that supplies the sheath fluid to a nozzle; an external sheath fluid container that supplies the sheath fluid to the internal pressurized sheath fluid reservoir, and that can be removed for resupplying the sheath fluid to the sheath container; a pump that continuously supplies the sheath fluid from the external sheath fluid container to the internal pressurized sheath fluid container to maintain a level of the sheath fluid in the internal pressurized reservoir substantially constant by substantially matching an in-flow rate of the sheath fluid from the external sheath fluid container to the internal pressurized sheath fluid reservoir with an out-flow rate of the sheath fluid from the internal pressurized sheath fluid reservoir, unless the external sheath fluid container has been removed for resupplying the sheath fluid; a compressor that supplies a source of compressed air; an air regulator that regulates the compressed air that is connected to the internal pressurized sheath fluid reservoir to supply regulated pressurized air to the internal pressurized sheath fluid reservoir; an air pressure controller that controls the regulated pressurized air, and increases the pressure of the regulated pressurized air whenever the level of the sheath fluid in the internal pressurized sheath fluid reservoir falls below a preselected level, and decreases the pressure whenever the level is increasing, so as to maintain a substantially constant pressure and a substantially constant velocity of the sheath fluid that exits the internal pressurized sheath fluid reservoir.

DETAILED DESCRIPTION OF THE EMBODIMENTS

Figure 1:
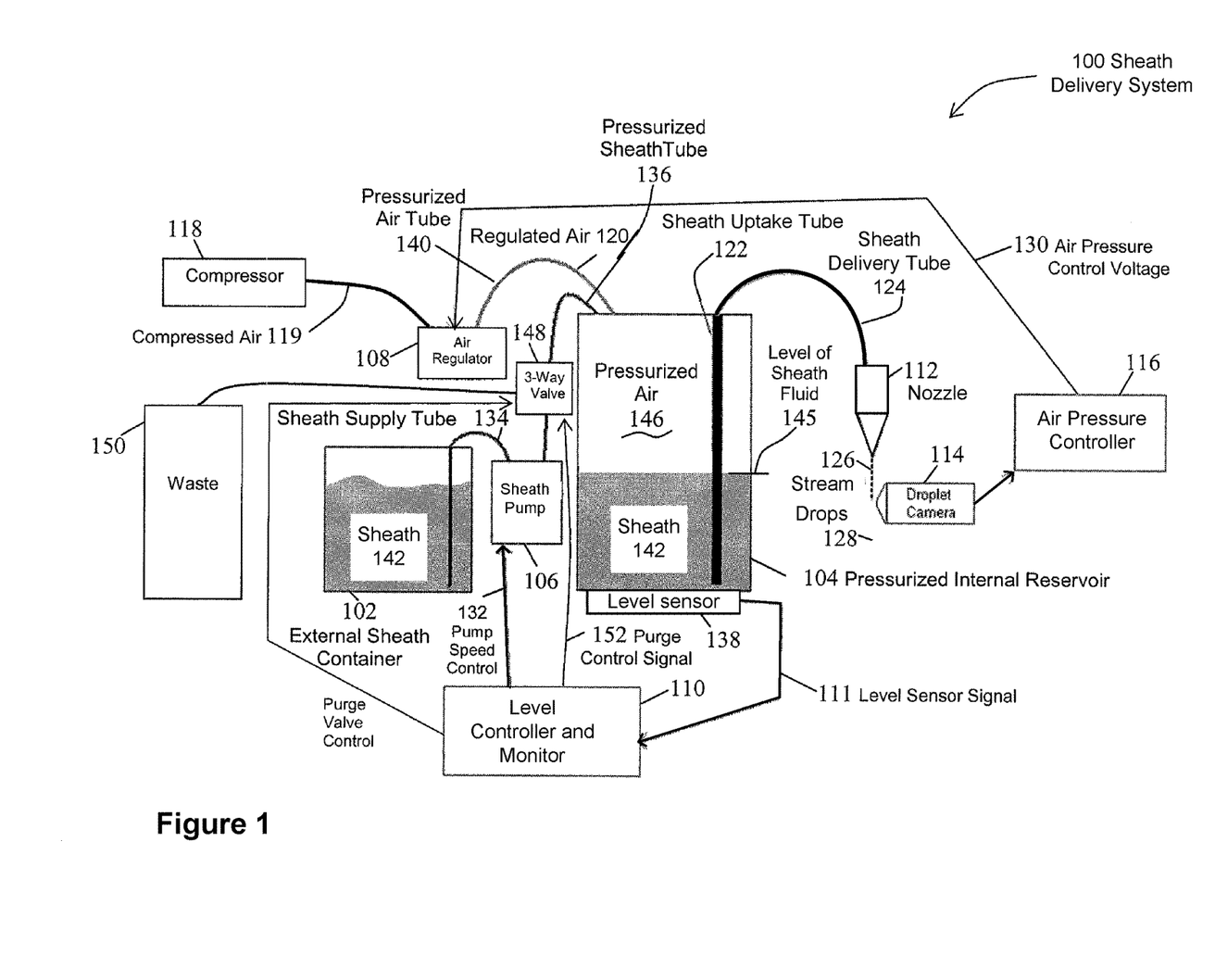
FIG. 1 is a schematic illustration of one embodiment of a sheath delivery system.

FIG. 1 is a schematic illustration of a sheath delivery system 100. The sheath delivery system 100 includes an external sheath container 102 that provides sheath fluid to an internal pressurized reservoir 104. As disclosed below, the external sheath container 102 can be removed by a user and refilled or replaced without stopping the operation of the sheath delivery system 100, while maintaining a substantially constant pressure on the sheath fluid that is delivered through nozzle 112.

For flow cytometers to operate properly, it is important that the stream 126, through nozzle 112 has a consistent velocity, which is dependent upon the pressure of the sheath fluid 144 in the sheath delivery tube 124. Otherwise, the flow cytometer must be continuously calibrated. Some systems that supply sheath fluid in flow cytometers have utilized large tanks to avoid the problem of shutting down the system when additional sheath fluid is needed. These large tanks are heavy and expensive. Furthermore, the change in the fluid height in these large tanks during operation results in considerable pressure changes between a full and nearly empty container. The pressure of the fluid that is supplied to the nozzle is the pressure supplied by pressurized air in the tank and the pressure that is supplied by the height of the fluid in the tank. In some systems, the level of the fluid can change by as much as twelve inches between a full and nearly empty container. This is a change of approximately 0.5 psi. If the sheath pressure is approximately 30 psi, the change in pressure resulting from the fluid can be as much as a 1.7 percent change in the pressure of the sheath fluid delivered to the nozzle. Additionally, air regulators that supply pressurized air to the tank may drift over time, and the air pressure in a pressurized tank may change, which also changes the pressure of the sheath fluid that is delivered to the nozzle. Some systems have utilized external sheath containers and pumps to pump the sheath fluid into an internal pressurized chamber for use during a short period of operation. However, such systems must be stopped during this filling procedure, which results in short run times and may necessitate recalibration of the system. These systems also do not account for changes in the pressure of the sheath fluid in the nozzle due to changes in the depth of the sheath fluid in the internal container. Other systems have attempted to resolve the short run time issue by using float switches in the internal container that turn a pump on and off to allow sheath fluid from an external sheath reservoir to flow into the internal container when the level drops by a predetermined amount in the internal container. However, this still results in intermittent, abrupt changes in the pressure of the sheath fluid flowing through the nozzle due to the level differences in the internal container, as a result of the non-continuous operation of the pump.

The embodiment of FIG. 1 operates using a continuous flow of sheath fluid into the pressurized internal reservoir 104 from the external sheath container 102. The sheath fluid provided by the external sheath container 102 is pumped at a rate that substantially matches the out-flow of the sheath fluid 144 through nozzle 112. In addition, if the level 145 of sheath fluid falls in the pressurized internal container because the flow rates are not matched, the in-flow of sheath fluid is slowly changed to make up for changes in the level 145 of the sheath fluid 144 in the pressurized internal container 104. By using a continuous in-flow of sheath fluid 142 from the external sheath container 102 that substantially matches the out-flow of sheath fluid 142 through nozzle 112, intermittent variations in the pressure of the sheath fluid 144 in the nozzle 112 do not occur.

The control loop (FIG. 2) for the process of matching flow rates between the input to the pressurized internal reservoir 104, and the out-flow to nozzle 112, are tightly controlled and dampened, so that pressure changes from the level 145 of the sheath fluid 144 are negligible. In addition, the control of the pressurized air 146 further reduces variations in the pressure of the sheath fluid 144 flowing through nozzle 112, as described in more detail below.

The system illustrated in the embodiment of FIG. 1 can utilize two control systems that separately control the level 145 of the sheath fluid 144 in the internal container 104, and the air pressure of the pressurized air 146 that is supplied by compressor 118 and air regulator 108. Utilizing these two control systems, a substantially consistent pressure of the sheath fluid can be provided to the nozzle 112. Since the two control loops utilize feedback from different sources, i.e., the level 145 of sheath fluid 144 and the velocity of the sheath fluid stream 126, the two separate systems can work in concert to automatically provide a substantially constant pressure of sheath fluid to the nozzle 112. The control system that controls the air pressure in the pressurized internal reservoir may be used either on a constant basis in concert with the level control system, or simply when there is a hot swap of the external sheath container, as explained in more detail below.

As illustrated in FIG. 1, sheath pump 106 pumps sheath fluid 142 into the pressurized internal reservoir 104 to provide a supply of sheath fluid 144 in the pressurized internal reservoir 104. Air regulator 108 provides regulated air 120 to the pressurized internal reservoir 104 to produce a supply of pressurized air 146 in the pressurized internal reservoir 104. Pressurized air tube 140 delivers the pressurized air from the air regulator 108 to the pressurized internal reservoir 104. Compressor 118 provides the compressed air 119 to the air regulator 108. Sheath supply tube 134 supplies the sheath fluid 142 to the sheath pump 106. Pressurized sheath tube 136 provides the sheath fluid from the sheath pump 106 to the pressurized internal reservoir 104. Level controller/monitor 110 comprises an electronic controller that generates a pump speed control 132 that is applied to the sheath pump 106. Level controller/monitor 110 receives a level sensor signal 111 from the level sensor 138. Level sensor 138 can comprise any type of level sensor. As illustrated in the embodiment of FIG. 1, level sensor 138 comprises an ultrasonic detector that is disposed at the bottom of the pressurized internal reservoir 104 which measures the height of the sheath fluid 144 in the pressurized internal container 104 with a 0.5 mm resolution. The level sensor signal 111 generated by level sensor 138 is applied to the level controller/monitor 110, which controls the sheath pump 106 via pump control speed signal 132 to maintain a substantially constant level of the sheath fluid 144 in the pressurized internal reservoir 104 in the manner described with respect to FIG. 2.

Sheath uptake tube 122, illustrated in FIG. 1, provides the pressurized sheath fluid 144 from the bottom of the pressurized internal reservoir 104 and delivers the pressurized fluid through the sheath delivery tube 124 to the nozzle 112. In one example, the pressurized air 146 may be pressurized to approximately two atmospheres, which is approximately 30 psi. The pressure of the pressurized air 146 is added to the pressure of the sheath fluid 144, which is dependent upon the level 145 of the sheath fluid 144 in the pressurized internal reservoir 104. In round numbers, one atmosphere is about 15 psi. The sheath fluid 144, in round numbers, provides a pressure of about ½ psi per each foot of depth of the sheath fluid 144. Accordingly, the pressure of the sheath fluid 144 in the sheath delivery tube 124 is the pressure of the pressurized air 146 together with the pressure created by the sheath fluid 144 in accordance with the level 145 of the sheath fluid 144 in the pressurized internal reservoir 104 minus any changes in fluid height.

A substantially constant pressure of the sheath fluid 144 in the sheath delivery tube 124 of FIG. 1 can be achieved by carefully maintaining a substantially constant level 145 of the sheath fluid 144 in the pressurized internal reservoir 104, as well as maintaining a substantially constant pressure of the pressurized air 146. Air pressure controller 116 generates an air pressure control voltage 130 that operates the air regulator 108. The regulated air 120 is supplied to the pressurized internal reservoir 108 via the pressurized air tube 140. Droplet camera 114 determines the position of the bottom of the stream, which corresponds to the location of the breakoff point of the droplets from stream 126 into drops 128. As explained in more detail with respect to FIG. 3, the location of the breakoff point of the drops 128 is indicative of the velocity of the stream 126, which is dependent upon the pressure of the sheath fluid 144 that is delivered to nozzle 112. The droplet camera 114 provides the graphic data to the air pressure controller 116 that processes that image data to generate the air pressure control voltage 130. Air pressure controller 116 generates an air pressure control voltage 130 to compensate for drift in the air pressure of the pressurized air 146 due to drift of the operation of the air regulator 108 and compressor 118, as explained in more detail with respect to FIG. 3.

As also illustrated in FIG. 1, a three-way valve 148 is connected to the pressurized sheath tube 136. During normal operation, the three-way valve 148 causes sheath fluid 142, from external sheath container 102, to be directed into the pressurized internal reservoir 104 via pressurized sheath tube 136. However, bubbles may form in the sheath supply tube, causing an airlock in the sheath pump 106. Airlocks of the sheath pump 106 may be created when air bubbles enter the sheath supply tube 134. This may occur when the external sheath container 102 is removed from the system and refilled with sheath fluid 142 or, the external sheath container 102 is replaced with a fill container, during a process referred to as a "hot swap," which is described in more detail with respect to FIG. 3. Since the sheath pump 106 is pumping the sheath fluid 142 into pressurized internal reservoir 104, that has a pressure on the order of 2 atmospheres, any air bubbles that enter the sheath pump 106 from the sheath supply tube 134 can easily create an airlock in the sheath pump 106. In order to clear the airlock, the three-way valve 148 is switched, so that the fluid from the sheath pump is directed into a waste disposal 150 that is at the ambient atmospheric pressure. Sheath pump 106 has sufficient power to clear an airlock by pumping the sheath fluid 142 into an ambient pressure waste disposal 150, but may not have sufficient power to clear airlocks into the multiple atmosphere pressurized air 146. Hence, by directing the output of the sheath pump 106 to an ambient atmospheric pressure, the airlock can be cleared.

Also, as illustrated in FIG. 1, if the level controller/monitor receives a level sensor signal 111 from the level sensor 138 that indicates that the level 145 of the sheath fluid 144 in the pressurized internal reservoir 104 is going down at a rate that is more than should be observed by the level sensor 138 for the rate at which the sheath pump 106 is being operated, the three-way valve 148 is activated to clear an airlock. In other words, the sheath pump 106 is provided a pump speed control 132, which is a voltage that is a percentage of the full voltage at which the sheath pump 106 operates. A comparison of the voltage of the pump speed control 132 with the level sensor signal 111 can indicate that an airlock may exist in the sheath pump 106, which can be used to trigger the level controller/monitor 110 to generate the purge control signal 152.

Figure 2:
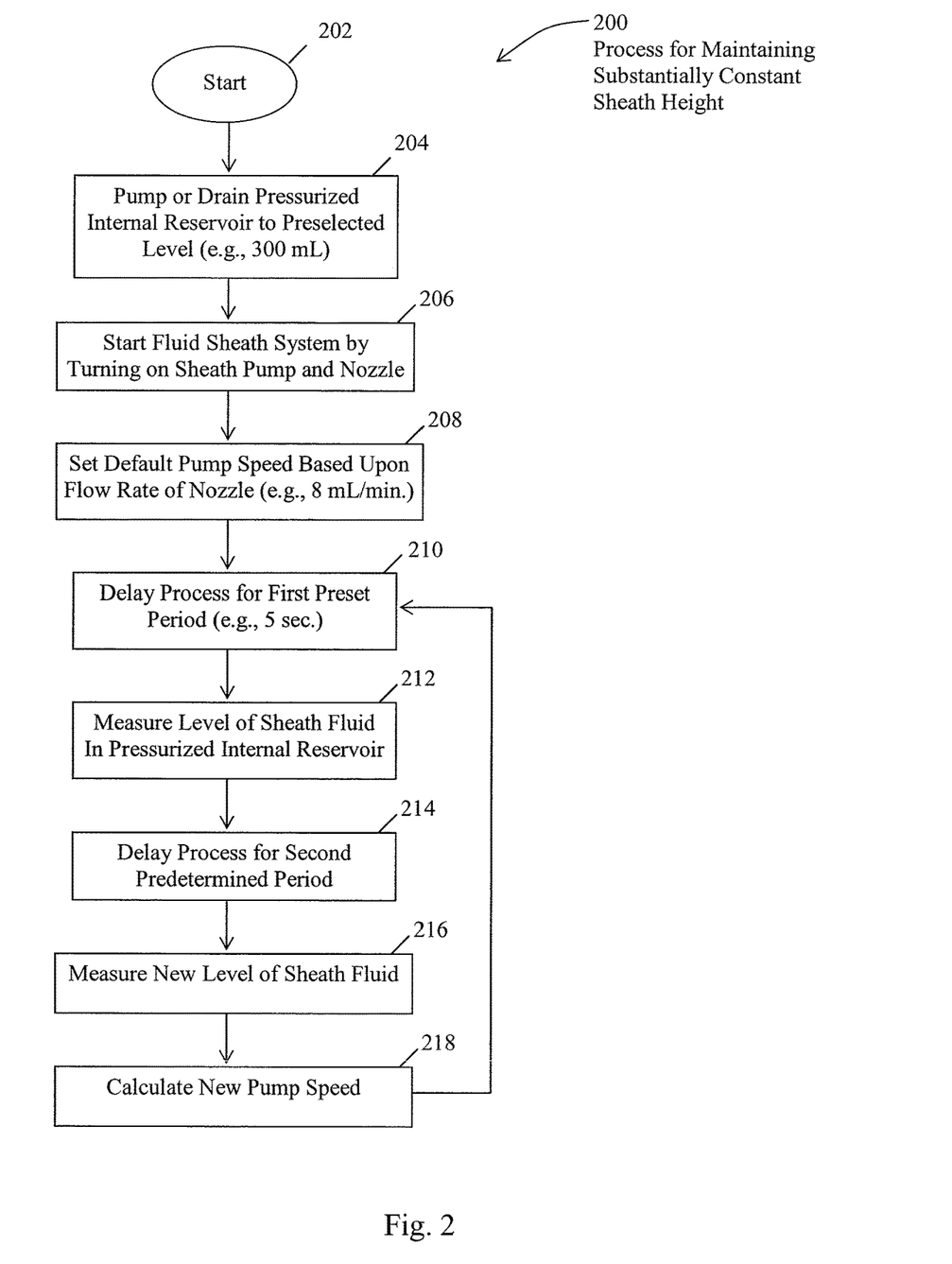
FIG. 2 is a flow diagram illustrating a process for maintaining a substantially constant sheath height.

FIG. 2 is a flow chart 200 that illustrates the process for maintaining a substantially constant level 145 of the sheath fluid 144. At step 202, the process starts. At step 204, the internal reservoir is pumped or drained to a preselected level, such as 300 ml. This occurs prior to the start of operation of the flow of sheath fluid 144 through nozzle 112. At step 206, the sheath pump 106 is started and the compressor 118 is started, to raise the level of the pressurized air 146 to a desired preset level. At this point, fluid sheath 144 begins to flow through the nozzle. Almost simultaneously, at step 208, the sheath pump 106 is set to a default pump speed, based upon an empirically derived flow rate of the nozzle at the selected level 145 of sheath fluid 144 and air pressure of pressurized air 146. In one example, the flow rate through the nozzle 112 is estimated to be 8 mL/min at a level of 300 mL and a pressure of 30 psi. The default pump speed is selected in an attempt to match the flow rate through the nozzle, i.e., 8 ml/min. In that regard, empirical data regarding the flow rate of nozzle 112 can be collected. Of course, other ways of initially estimating the amount of sheath fluid delivered by the nozzle 112 can be used to set the default pump flow rate to substantially match the rate of flow of sheath fluid through nozzle 112.

The process of setting the default pump speed, at step 208 of FIG. 2, involves the use of Equation 1.

Pump control percentage=(pump rate*constant related to pump operation)+offset voltage of pump. (Equation 1)

The pump control percentage is a percentage of the full operation of the pump. With the operating range of a pump, most pumps have a linear response to applied voltage levels. However, most pumps have an offset voltage. The offset voltage is the voltage at which the pump starts to operate and pump fluid. For example, the sheath pump 106 utilized in the embodiment of FIG. 1, does not start pumping until ten percent of the full operating voltage of the pump is applied to the pump. For example, in an example of the embodiment of FIG. 1, the full operating voltage of the sheath pump 106 is 5 volts. From empirical data, it was determined that sheath pump 106 starts pumping fluid when 0.5 volts is applied to the sheath pump 106. The voltage of 0.5 volts is ten percent of the five volts that causes the sheath pump 106 to operate at full capacity. Hence, the offset of sheath pump 106 is 10%. From 0.5 volts to 5.0 volts, the output of the sheath pump 106 is substantially linearly related to the voltage. Because of this linear relationship, equation 1 can be correlated to the standard Equation 2.

$$y=m+b$$ (Equation 2)

In equation 2, b is the offset, which was empirically determined to be 10%. The slope of the curve (m) for the sheath pump 106 of FIG. 1 can also be empirically determined and was found, in one example, to be 1.25 from data collected by operating the sheath pump 106. This results in Equation 3, which is created from the collected empirical data for sheath pump 106 of the embodiment of FIG. 1.

Pump Control Percentage=1.25*Pump Flow Rate+10 (Equation 3)

From Equation 3, it can be determined that an initial default pump flow rate of 8 mL/min results in a pump control percentage of 20%, which equates to 1 volt that should be applied to sheath pump 106. Other pumps have different characteristics and empirical data must be collected for each pump to verify Equation 3. However, it can be assumed that pumps from the same manufacturer, with the same model number, may have very similar operating characteristics, such that Equation 3 is most probably valid for same make and model number pumps. Initial default pump float rates can normally be used for pumps that are the same make and model, so that empirical data does not have to be collected for each pump.

At step 210 of FIG. 2, the process is delayed for a preset period, for example, 5.0 seconds. This delay is used to allow the flow rate to stabilize. The level 145 of the sheath fluid 144 is measured in the pressurized internal reservoir 104 at step 212. To suppress noise in the readings of level 145 of the sheath fluid 144, in one embodiment, 42 readings of the level sensor 138 are taken, the lowest five and the highest five readings are discarded and the mean value of the remaining 32 readings is used as the level 145 of the sheath fluid. This process removes noise and aberrant readings. After the level has been measured, the system delays for a second predetermined time period at step 214. The system illustrated in the embodiment of FIG. 1 delays for a second time period of 30 seconds. This delay is somewhat substantial so that a trend can be observed in the level 145 of the sheath fluid 144. At the end of the second predetermined time period, a new level 145 of the sheath fluid is measured at step 216. At step 218, a new pump speed is calculated. In order to calculate a new pump speed, the differential actual outflow of fluid must be calculated. Assuming the level has decreased, Equation 4 calculates the differential actual outflow as follows:

Differential Actual Outflow=Pump Rate+Level Decrease*2     (Equation 4)

The level decrease is multiplied by two since the change in fluid level occurs over a 30 second period, and the data is indicated on a per minute basis.

For example, if the initial pump speed is set at 8 mL per minute and the level decreases by 0.25 mL in the 30 second delay period, the true differential outflow during that period is 8.5 mL per minute, which is calculated as:

Differential Actual Outflow=8.0 (the pump rate)+ 0.25 (the level decrease)*2=8.5     (Equation 5)

The new pump speed is the modified pump speed that is calculated to slowly reduce the difference in the level 145 of the sheath fluid 144 from the desired level. In order to calculate the new pump speed, Equation 6 should be used:

New Pump Speed=Differential Actual Outflow+Error/2     (Equation 6)

The error is calculated as the difference between the desired level minus the new level. If the desired level is 300 mL and the new level is 299 mL, the error is equal to 1 mL. The system attempts to return to the new level within a period of 2 minutes, even though the sampling rate is every 30 seconds. That accounts for the "2" in Equation 6. At the end of every 30 second period, a new pump speed is calculated based upon a pump speed that would return the new level to the desired level in a 2 minute period. In this manner, the target of the new pump speed will not be overshot and the control system is adequately dampened to provide a new pump speed that will slowly return to the desired level. In the example given above, the ideal level was 1 mL low, which is the error. The error, 1 mL divided by 2 minutes equals 0.5 mL/minute. Inserting these values in Equation 6:

New Pump Speed=8.5+0.5=9.0 mL/minute     (Equation 7)

The 9.0 mL/minute is then converted to a pump control percentage using the pump control equation (Equation 3). In this case:

Pump Control Percentage=1.25×9.0+10=21.25%     (Equation 8)

The actual voltage that is applied to the pump is given as follows:

Voltage Applied to Pump=21.25%×5.0 volts=1.0625 volts     (Equation 9)

The process of FIG. 2 then returns to step 210 and delays for the first preset period.

Of course, other types of controllers can be used, such as standard PID controllers. Proportional integral derivative controllers (PID controllers) use a generic control feedback that is widely used in industrial control systems. A PID controller calculates an error value as the difference between a measured process variable and a desired set point. The controller attempts to minimize the error by adjusting the process control inputs. The PID controller calculation involves three separate parameters that comprise the proportional, the integral and the derivative values. Heuristically, these values can be represented in terms of time wherein P depends on the present error, I depends on the accumulation of past errors and D is a prediction of future errors, based on the current rate of change. A weighted sum of these three values is used to adjust the process, in this case, the voltage applied to sheath pump 108. The accuracy of the PID controllers is very much dependent upon the weighting of each of the PID values.

Figure 3:
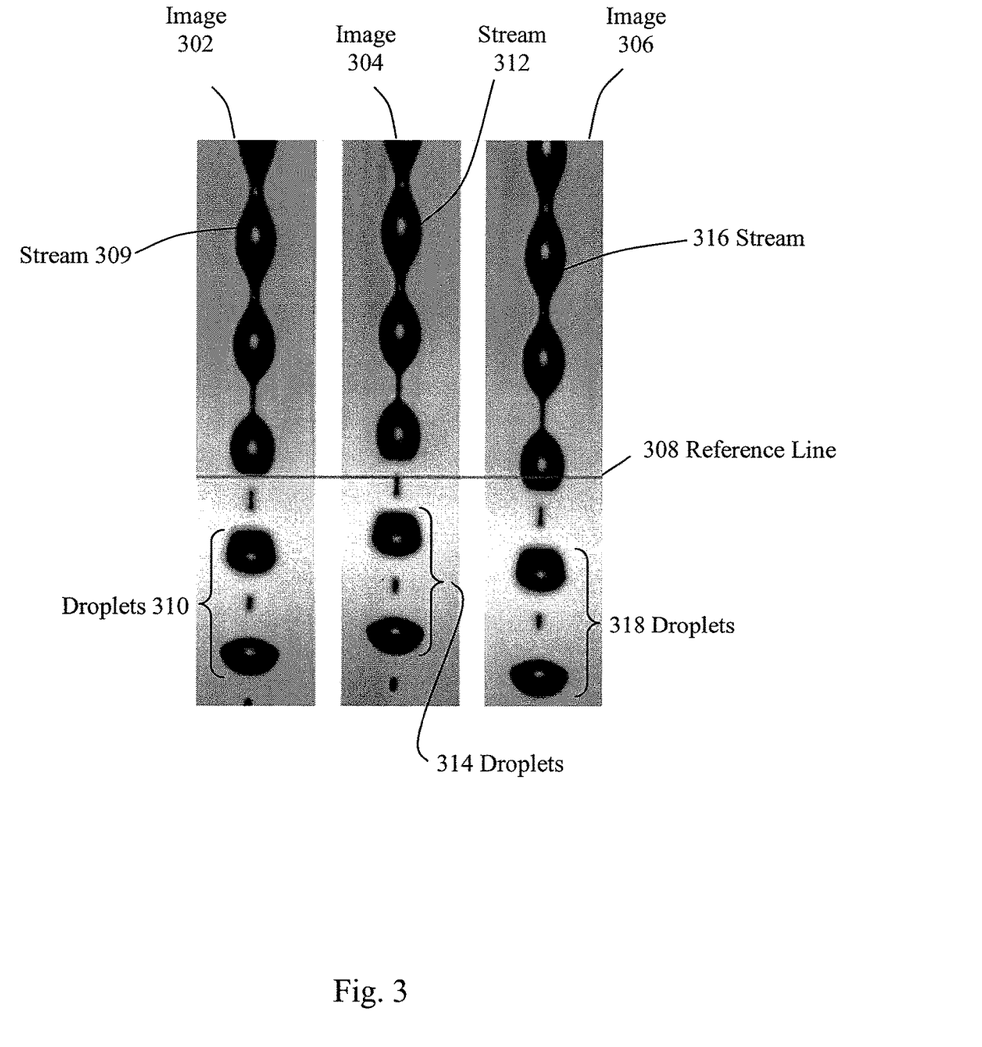
FIG. 3 illustrates images of the breakoff point of droplets from streams that indicate the velocity of the streams.

FIG. 3 illustrates images 302, 304, 306 of the breakoff point of droplets 310, 314, 318, from streams 309, 312, 316, respectively, that are taken by the camera 114 and sent to the air pressure controller 116. As illustrated in FIG. 3, an image 302 shows droplets 310 breaking away from stream 309 at a reference line 308. Reference line 308 is considered a reference for a desired stream velocity that is produced by stream 309. A slower velocity stream 312 is illustrated by image 304, which is the result of a pressure decrease of the stream 312, such that the breakoff point of the droplets 314 from the stream 312 is above the reference line 308 at a higher location. Image 306 shows stream 316, which has a higher velocity, which is the result of a higher pressure on stream 316, resulting in the droplets 318 breaking off from stream 316 at a lower point below the reference line 308. As such, the velocity of the stream and the resultant pressures on the streams can be determined by identifying the breakoff point of the droplets from the stream. As described above, air regulator 108 sets the pressure of the pressurized air 146 in the pressurized internal reservoir 104. Since air regulators may tend to drift over time and with temperature during operation, the droplet camera 114 can be used to accurately determine if there is a change in air pressure based upon the velocity of the stream, as indicated by the images 302, 304, 306 provided by the droplet camera 114. A strobe light may be used with the droplet camera 114 that has a fixed phase relative to the sign wave of a piezoelectric vibrator (not shown) that is used to create droplets, as illustrated in FIG. 3. The air pressure controller 116 operates by storing the location of the reference line 308. When the bottom of the stream moves below the reference line 308, as indicated by higher velocity stream 312, there is a pressure increase and the pressure of the pressurized air 146 is decreased by 0.01 psi per second. Likewise, if the bottom of the stream moves above the reference line 308, the pressure of the pressurized air 146 is increased by 0.01 psi every second. These changes are slow moving changes in the pressurized air 146 that do not radically change the pressure, which could negatively affect the sorting process. Of course, other types of controllers can be used including different values. For example, a PID controller could be used to calculate appropriate changes in air pressure.

Since the embodiment of FIG. 1 is able to control the pressure of the pressurized air 146, the external sheath container 102 can be removed and refilled without stopping the sheath delivery system 100 of FIG. 1. Removal of the external sheath container 102 for refilling is referred to as a hot swap mode, since the sheath fluid system continues to operate. In the hot swap mode, the sheath pump 106 is stopped completely for the period of time that it takes to remove the external sheath container 102, refill the external sheath container 102, and replace the external sheath container 102 in the sheath delivery system 100 of FIG. 1. The user of the sheath delivery system 100 removes the external sheath container 102 and either fills the external container or replaces the external container with a new external container that is filled with sheath fluid. With an average outflow of 8 mL per minute, the sheath fluid level will slowly decrease in the internal pressurized container during the hot swap mode. The change in pressure from the sheath fluid 144 is compensated for by increasing the pressure of the pressurized air 146. The lower pressure of the sheath fluid during the hot swap mode is detected as the slower velocity image 304. When the slower velocity image 304 is detected, the air pressure controller 116 continues to increase the air pressure at a rate of 0.01 psi per second by applying the air pressure control voltage 130 to the air regulator 108. The air pressure in the internal pressurized sheath fluid reservoir continues to increase until a new bottle of sheath fluid or refilled bottle of sheath fluid 142 is placed in the sheath delivery system 100. Once the new bottle is reattached, the user can exit the hot swap mode. At that point, the sheath pump 106 is restarted, and sheath fluid 142 is pumped into the pressurized internal reservoir 104 at a rate that is calculated by the level of the controller/monitor 110 in the manner set forth above. As the sheath fluid enters the pressurized internal reservoir 104, the air pressure controller 116 slowly reduces the pressure of the pressurized air 146 in the internal reservoir 104 to maintain a substantially constant pressure on the sheath fluid 144 exiting internal reservoir 104 that travels through the nozzle 112. In this manner, the sheath pressure of the sheath fluid 144 that flows through the nozzle 112 is carefully regulated within the requirements for stable sorting to provide a substantially constant pressure.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A sheath fluid system for controlling pressure of a sheath fluid in a flow cytometer, the sheath fluid system comprising:
   a reservoir configured to contain both a volume of sheath fluid and a volume of positively pressurized air and fluidically connected to a nozzle;
   an external container configured to contain sheath fluid;
   a pump fluidically interposed between the external container and the reservoir and configured to pump the sheath fluid from the external container to the reservoir;
   an air regulator configured to regulate the volume of the positively pressurized air in the reservoir;
   a compressor configured to supply compressed air to the air regulator;
   an optical sensor configured to detect droplet locations of the sheath fluid flowing out of the nozzle;
   a level controller configured to:
      continuously pump, using the pump, the sheath fluid from the external container into the reservoir to maintain a substantially constant sheath fluid level in the reservoir so that an in-flow rate of sheath fluid flowing into the reservoir is substantially equal to an out-flow rate of the sheath fluid flowing out of the nozzle, and
      adjust the in-flow rate of the sheath fluid flowing into the reservoir by adjusting a pump speed of the pump whenever the substantially constant sheath fluid level changes; and
   an air pressure controller configured to:
      determine the out-flow rate of fluid flowing out of the nozzle based on data from the optical sensor, and
      control the pressure of the volume of positively pressurized air in the reservoir based upon the determination, so that the out-flow rate of fluid flowing out of the nozzle, as determined by the optical sensor, remains substantially constant.

2. The sheath fluid system of claim 1, wherein the air pressure controller is further configured to:
   detect a vertical location of a breakoff point at which droplets separate from a stream of fluid exiting the nozzle of the flow cytometer;
   compare the vertical location with a desired vertical location; and
   adjust the pressure of the volume of positively pressurized air in the reservoir to cause the vertical location of the breakoff point to substantially match the desired vertical location.

3. The sheath fluid system of claim 2, wherein:
   the optical sensor is a droplet camera configured to record images of the stream, and
   the process of detecting a vertical location of a breakoff point comprises using the images of the stream recorded by the droplet camera.

4. The sheath fluid system of claim 1, wherein the level controller is further configured to set a default in-flow rate by estimating the out-flow rate at which the sheath fluid is flowing out of the reservoir.

5. The sheath fluid system of claim 1, wherein:
   the level controller is further configured to determine a level of the sheath fluid in the reservoir, and
   adjusting the in-flow rate of the sheath fluid flowing into the reservoir is based, at least in part, on the determination of the level of the sheath fluid in the reservoir.

6. The sheath fluid system of claim 5, further comprising a level sensor configured to determine a level of a fluid in the reservoir, wherein determining the level of the sheath fluid in the reservoir is based on a level sensor signal generated by the level sensor.

7. The sheath fluid system of claim 6, wherein the level sensor is an ultrasonic detector.

8. The sheath fluid system of claim 1, wherein the level controller is further configured to:
   take a plurality of measurements of a height of the sheath fluid in the reservoir, and
   determine whether a trend in the height of the sheath fluid has been observed.

9. The sheath fluid system of claim 8, wherein adjusting the in-flow rate of the sheath fluid flowing into the reservoir is performed in response to determining that a trend in the height of the sheath fluid has been observed.

10. The sheath fluid system of claim 1, further comprising:
    a three-way valve fluidically interposed between the pump and the reservoir; and
    a waste container fluidically connected to the three-way valve, wherein the level controller is further configured to:
       determine that an airlock has occurred in the pump, and
       switch the three-way valve to cause the pump to flow the sheath fluid from the external container into the waste container.

11. The sheath fluid system of claim 10, wherein determining that the airlock has occurred in the pump comprises determining that the out-flow rate of the sheath fluid from the reservoir is greater than the in-flow rate of the sheath fluid to the reservoir.

12. The sheath fluid system of claim 1, wherein the level controller is further configured to adjust the sheath in-flow rate in response to a dampened feedback control loop.

13. The sheath fluid system of claim 12, wherein:
the level controller is further configured to perform the dampened feedback control loop, and
the dampened feedback control loop comprises:
(a) measuring a first level of the sheath fluid in the reservoir;
(b) measuring, after measuring the first level of the sheath fluid in the reservoir by a first time period, a second level of the sheath fluid in the reservoir; and
(c) calculating a pump speed based on the first level and the second level of the sheath fluid in the reservoir.

14. The sheath fluid system of claim 13, wherein the level controller is further configured to repeat (a) through (c).

15. The sheath fluid system of claim 13, wherein calculating the pump speed comprises determining an out-flow rate of the sheath fluid from the reservoir based on the pump speed and a change in the level of the sheath fluid in the reservoir between the first level and the second level of the sheath fluid in the reservoir.

16. The sheath fluid system of claim 1, wherein:
the level controller includes a proportional integral derivative controller, and
the process of adjusting the in-flow rate is performed in response to the proportional integral derivative controller.

17. The sheath fluid system of claim 1, wherein the external container is configured to be refilled with sheath fluid.

18. The sheath fluid system of claim 1, wherein:
the external container is configured to be fluidically disconnected from the pump,
the level controller is further configured to reduce, at least when the external container has been fluidically disconnected from the pump, the in-flow rate of the sheath fluid flowing into the reservoir to zero, and
the air pressure controller is further configured to increase, at least when the external container has been fluidically disconnected from the pump and at least when the in-flow rate of the sheath fluid flowing into the reservoir is zero, the pressure of the volume of positively pressurized air based upon the determination, so that the out-flow rate of fluid flowing out of the nozzle, as determined by the optical sensor, remains substantially constant.

19. The sheath fluid system of claim 18, wherein:
the external container is configured to be fluidically connected to the pump after being fluidically disconnected from the pump,
the level controller is further configured to increase, at least when the external container has been fluidically connected to the pump, the in-flow rate of the sheath fluid flowing into the reservoir to an in-flow rate that is greater than the out-flow rate of fluid flowing out of the nozzle, and
the air pressure controller is further configured to reduce, at least when the external container has been replaced and when the in-flow rate of the sheath fluid flowing into the reservoir is greater than the out-flow rate of fluid flowing out of the nozzle, the pressure of the volume of positively pressurized air based upon the determination, so that the out-flow rate of fluid flowing out of the nozzle, as determined by the optical sensor, remains substantially constant.

* * * * *